United States Patent [19]

Zhang et al.

[11] Patent Number: 5,364,993
[45] Date of Patent: Nov. 15, 1994

[54] SELECTIVE FUNCTIONALIZATION OF FULLERENES

[75] Inventors: Zhenyu Zhang, New York, N.Y.;
Warren Ruderman, Demarest, N.J.;
James R. Fehlner, Salem Township, Wayne County, Pa.

[73] Assignee: Inrad, Inc., Northvale, N.J.

[21] Appl. No.: 7,305

[22] Filed: Jan. 21, 1993

[51] Int. Cl.$^5$ .................. C07C 17/00; C07C 19/00; C07C 21/00
[52] U.S. Cl. .................. 570/187; 568/633; 568/634; 568/811; 568/812
[58] Field of Search ................ 570/187; 568/633, 634, 568/811, 812

[56] References Cited

PUBLICATIONS

Salig et al., "J. Amer. Chem. Soc." vol. 113, p. 5475 (1991).
Bausch et al., "J. Amer. Chem. Soc." vol. 113, p. 3205 (1991).
Vasallo et al., "J. Amer. Chem. Soc." vol. 113, p. 7820 (1991).
Olah et al., "J. Amer. Chem. Soc." vol. 113, pp. 9385–9388 (1991).
Loy et al., "J. Amer. Chem. Soc" vol. 114, p. 3977.
Hammond et al., "ACS Symp. Series 481", Wash., D.C. 1992, p. 161.
Kroto, H. W., et al., Nature 318, 162 (1985).
Kräschmer, W., et al., Nature 347, 354 (1990).
Haddon, R. C., et al., Nature 350, 320 (1990).
Hebard, A. F., et al., Nature 350, 600 (1990).
Allemand, P. M., et al., Science 253, 301 (1991).
Regueiro, M. N., et al., Nature 355, 237 (1992).
Wang, X. K., et al., Appl. Phys. Lett. 60, 810 (1992).
Gong, Q., et al., Appl. Phys. 71, 3025 (1992).
Tutt, L. W., Nature 356, 225 (1992).
*Business Week*, p. 101, May 11, 1992.
Hawkins, J. M., et al., Org. Chem. 55, 6250 (1990).
Heyman, D., Carbon 29, 684 (1991).
Diederich, F., et al., Science 252, 548 (1991).
Sunderlin, L. S., et al., J. Am. Chem. Soc. 113, 5489 (1991).
Haufler, R. E., et al., J. Phys. Chem. 94, 8634 (1990).
Creegan, K. M., et al., J. Am. Chem. Soc. 114, 1103 (1992).
Tebbe, F. N., J. Am. Chem. Soc., 113, 9900 (1991).
Wood, J. M., et al., J. Am. Chem. Soc. 113, 5907 (1991).
Hawkins, J. M., et al., Science, 512, 312 (1991).
Fagan, P. J., et al., Science 252, 1160 (1991).
Arbogast, J. W., et al., J. Phys. Chem. 95, 11 (1991).
Arbogast, J. W., et al., J. Am. Chem. Soc. 114, 2277 (1992).
Suzuki, T., et al., Science 254, 1186 (1991).
Krusic, P. J., et al., Science 254, 1183 (1991).
Baum, R. M., Chem. & Eng. News, Dec. 16, 1991, p. 17.
Breck, D. M., Zeolite Molecular Sieves, Wiley & Sons, New York, 1973.
Turro, N. J., Pure & Appl. Chem. 58, 1219 (1986).
Turro, N. J., et al., Photochemistry in Organized and Constrained Media, Ramamurthy, V., ed. VCH: New York, 1991, p. 1.
Ramamurthy, V., Photochemistry in Organized and Constrained Media, Ramamurthy, V., ed. VCH: New York, 1991, 429.
Turro, N. J., et al., J. Org. Chem. 53, 3731 (1988).
Bhatia, S., Zeolite Catalysis: Principles and Applications, CRC Press, Boca Raton, 239 (1990).
Keizer, P. N., et al., J. Phys. Chem. 95, 7117 (1991).
Kroto, H. W., et al., Chem. Rev. 91, 1213 (1991).
Baum, R. Chem. & Eng. News Mar. 23 (1992) p. 6.

*Primary Examiner*—Werren B. Lone
*Attorney, Agent, or Firm*—Stroock & Stroock & Lavan

[57] ABSTRACT

Fullerenes are selectively functionalized by adsorbing fullerene molecules on molecular sieves such as zeolites as the first step in a desired functionalizing reaction and then adding functional groups or compounds to the fullerenes within the molecular sieves. An improved reactor for fullerene material is thereby available. Selectively functionalized fullerenes formed in accordance with the invention can also serve as precursors for further selectively functionalized products.

33 Claims, 9 Drawing Sheets

SELECTIVE FUNCTIONALIZATION OF FULLERENES

BACKGROUND OF THE INVENTION

The invention relates generally to fullerenes and more particularly to the selective addition of functional compounds and groups to fullerene molecules.

Fullerenes are a family of closed-shell carbon molecules with $C_{60}$ as the prototypical member. A $C_{60}$ molecule is depicted in FIG. 1. A technique for preparing and isolating macroscopic quantities of fullerenes was reported by Krätschmer et al., *Nature* 347 (354) (1990), the contents of which are incorporated herein by reference. Since that time, research on fullerenes has been of considerable importance for both its academic and commercial implications.

Research on fullerenes can generally be categorized into two different types. The first relates to the physical and material properties. For example, it has been discovered that when doped with a number of alkali metals, $C_{60}$ exhibits high temperature superconductivity, as reported by Haddon, et al., *Nature* 350 (320) (1990) and Hebard, et al., *Nature* 350 (600) (1990), the contents of which are incorporated herein by reference.

Other discovered properties of $C_{60}$ include (a) organic ferromagnetism when an organic reducing agent is added to $C_{60}$ as reported by Allemand, et al., *Science* 253 (301) (1991); (b) high resilience and stability as reported by Vasallo, et al., *J. Am. Chem. Soc.* 113(7820) (1991); (c) conversion to diamond by application of asymmetric pressure at room temperature as reported by Reguerito, et al., *Nature* 355 (237) (1002); (d) nonlinear optical properties as reported by Wang, et al., *Appl Phys. Lett.* 60 (810) (1992) and Gong, et al., *Appl. Phys.* 71 (3025) (1992); (e) optical limiting properties as reported by Tutt, *Nature* 356 (225) (1992); and (f) the trapping and separation of gases as reported by *Business Week*, p. 101, May 11, 1992. The contents of each of these references is incorporated herein by reference.

The second type of research relates to the chemistry of the fullerene molecules. Chemically, $C_{60}$ behaves similarly to electron deficient alkenes and is a mild oxidizing agent. The relatively high electronegativity of fullerenes is thought to be due to the pyracyclic character of certain inter-five-membered ring bonds. Chemical reactions of fullerenes that have been studied, include methylation, as reported by Bausch, et al., *J. Am. Chem. Soc.* 113 (3205) (1991); hydrogenation as reported by Haufler, et al., *J. Phys. Chem.* 94 (8634) (1990); fluoration as reported by Selig, et al., *J. Am. Chem. Soc.* 113 (5475) (1991); epoxidation as reported by Creegan, et al., *J. Am. Chem. Soc.* 114 (1103) (1992); halogenation as reported by Olah, et al., *J. Am. Chem. Soc.* 113 (9385) (1991) and Tebbe, et al. *J. Am. Chem. Soc.* 114 (3977) (1992); and nucleophilic addition as reported by Wudl, et al. *Fullerenes: Synthesis, Properties, and Chemistry of Large Carbon Clusters*, Hammond, et al. ACS Symp. Series 481, Washington, D.C. 1992, p. 161. The contents of each of these references is incorporated herein by reference.

Although the reactions discussed above have proved to be reproducible at the laboratory level, they have yet to show satisfactory commercial significance. These reactions were all carried out in homogeneous media. A common obstacle for these chemical reactions is the inability to achieve selective functionalization. The inability to control the production of byproducts continues to be the focus of considerable activity.

For example, the chlorination and bromination of $C_{60}$ yields a complex mixture of chlorinated products with up to 24 halogen atoms added to the $C_{60}$. The nucleophilic addition of amines to $C_{60}$ leads to multiple addition products. The copolymerization of $C_{60}$ and p-xylylene yields highly crosslinked polymers due to the multiple benzylation of $C_{60}$. A more detailed discussion of these reactions can be found in Olah, et al. *J. Am. Chem. Soc.* 113 (9385) (1991), Wudl. et al. *Fullerenes: Synthesis, Properties, and Chemistry of Large Carbon Clusters*, Hammond, et al. ACS Symp. Series 481, Washington, D.C. 1992, p. 161, and Loy, et al. J. Am. Chem. Soc. 114 (3977) (1992), the contents of which are incorporated herein by reference.

As is evident from the above, the inability to control these reactions, which produce a mixture which is very difficult to separate and characterize, diminishes the commercial value of these reactions and limits the commercial application of fullerene chemistry. Accordingly, a selective functionalization method is needed in order to fully develop the potentially rich chemistry of fullerenes in a more satisfactory manner.

SUMMARY OF THE INVENTION

Generally speaking, in accordance with invention, fullerenes are selectively functionalized by adsorbing fullerene molecules on molecular sieves such as zeolites as the first step in a desired functionalizing reaction and then adding functional groups or compounds to the fullerenes within the molecular sieves. An improved reactor for fullerene material is thereby available. For example, when $C_{60}$ is loaded on zeolite material and photochlorination is carried out, the chlorination reaction is much more selective than for reactions conducted in a conventional manner. Other selective functionalization reactions on molecular sieve material include photohalogenation, thermal halogenation, amination, free radical addition, copolymerization and aromatic addition. Thus, fullerene products with high levels of selectively functionalized molecules can be produced. Selectively functionalized fullerenes formed in accordance with the invention can also serve as precursors for further selectively functionalized products.

Accordingly, it is an object of the invention to provide a method for selectively functionalizing fullerenes.

Another object of the invention is to provide a fullerene reaction product with reduced byproducts and higher purity.

A further object of the invention is to provide an improved reactor for functionalizing fullerenes.

Still other objects and advantages of the invention will in part be obvious and will in part be apparent from the specification and drawings.

The invention accordingly comprises the several steps and the relation of one or more of such steps with respect to each of the others, the reactor embodying features of construction, combinations of elements and arrangements of parts which are adapted to effect such steps, and the product which possesses the characteristics, properties, and relation of constituents, all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
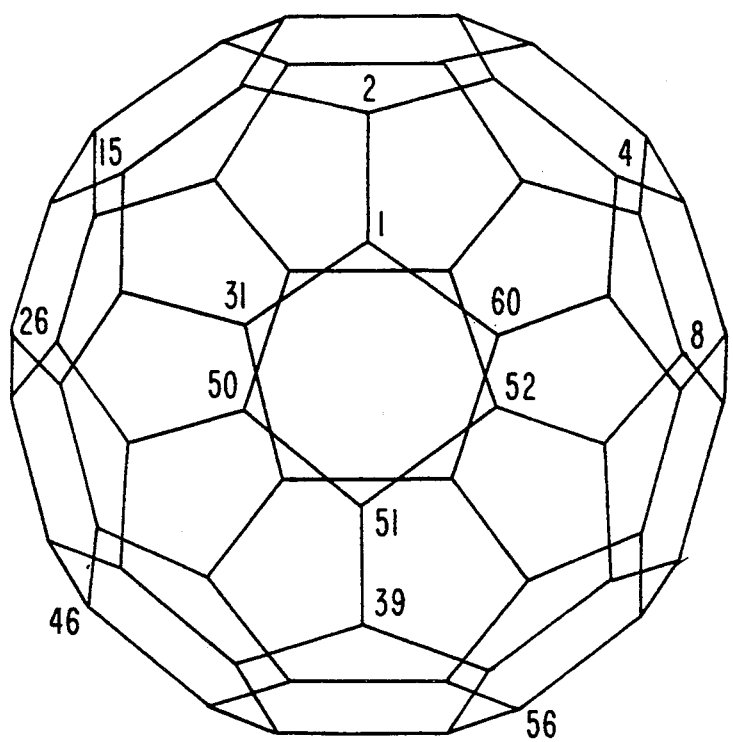
FIG. 1 shows a schematic representation of a $C_{60}$ fullerene molecule.

The selective functionalization of fullerenes can be achieved by first adsorbing fullerenes on molecular sieves such as zeolites. In gross solution chemistry, the attack of incoming reagent on fullerene molecules is completely random. However, it has been discovered that when fullerenes are adsorbed on molecular sieves such as zeolites, the geometry of the zeolite channels, pores and cages (hereinafter referred to as controlled spaces) prevents the random attack of incoming reagents on fullerenes because portions of the adsorbed fullerenes will be protected by the walls of the controlled spaces. Thus, relatively high selective functionalization, compared to that of conventional solution chemistry methods, can be achieved. It can also be possible to take advantage of the catalytic acid centers in the zeolite channels to initiate selective additions.

Control of fullerene chemistry will permit the production of many useful precursors for the production of fullerene-based products. For example, the addition of a single styrene molecule or derivative to $C_{60}$ could give a monomer for producing polymer chains with pendent $C_{60}$ molecules. The availability of techniques to selectively functionalize fullerenes will greatly advance progress towards the production of useful fullerene-based materials.

Molecular sieves are a class of materials which contain pores, channels and/or cages (controlled spaces) whose size is similar to that of many organic molecules. Preferred molecular sieve material has controlled spaces that are about 4 to 18 Å large. Accordingly, molecular sieves can differentiate between organic molecules by size and geometry.

Zeolites are an important type of molecular sieve material. Zeolites are porous crystalline aluminosilicates. Silicalite is an effective molecular sieve that does not contain significant amounts of aluminum. The typical composition of aluminosilicate zeolites can be represented by the following formula:

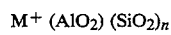

$$M^+ (AlO_2)(SiO_2)_n$$

wherein $M^+$ denotes exchangeable cations and n is the Si:Al ratio of the zeolite.

The framework structure of zeolites is based on an infinitely extending 3-dimensional network of $AlO_4$ and $SiO_4$ tetrahedra that are linked to each other by shared oxygen atoms. Zeolites contain controlled spaces with sizes in the range of about 4 to 13 Å. These controlled spaces are similar in size to many organic molecules and zeolites can adsorb many types of organic molecules. Two types of zeolites, NaX and NaY have a 3-dimensional network of pores and cages. The pores are linked to spherical cages called super cages in a tetrahedral configuration. The average pore size is about 7.5 Å and the diameter of the super cage is about 13 Å. Another type of zeolite, zeolite mordenite has 2-dimensional pores with diameters of about 7.0 and 2.8 Å. L has 1-dimensional pores with diameters of about 7.5 Å.

Each tetrahedral aluminum in the zeolite framework has a formal net negative charge. Accordingly, there must be a corresponding cation in the channel system. These cations are important in characterizing the properties of the zeolite material. If the cations are hydrogen ions (protons), the zeolite is referred to as being in the acidic form. In this form, it can serve as an acid catalyst for a number of different types of reactions.

The ultimate pattern of the substituted product is important in obtaining desirable materials. For example, the photochlorination of fullerenes is by a radical mechanism. In the free radical addition, the first radical can attack the double bond of the pyracyclene portion on the fullerene structure. It will be assumed herein that it attacks a carbon atom numbered 1 in FIG. 1. A $C_{60}$ numbering system has been described by Kroto, et al., *Chem. Rev.* 91 (121) (1991) and is adopted herein. The position of attack of the second radical is determined by the stability of the product's form. Certain positions will yield more stable resonance forms than others. One possibility is reaction with one of the adjacent carbons, numbered 2, 31 or 60. It is believed that the positions para to the point of substitution (4 and 15) are easily substituted.

It has been determined that if the first substituent on a fullerene molecule in a zeolite channel is large enough, it will effectively minimize a second attack on the same side of the molecule. If position 1 is thought of as one of the poles, any of the positions around the equator (positions 8, 26, 46 and 56, for example) of the $C_{60}$ molecule will be effectively blocked by the walls of the zeolite because the initial substituent will block any significant rotation. The most exposed positions on the opposite pole of the molecule, which will give stable products, are positions 39, 50 and 52. These three positions surround position 51 which is directly opposite from position 1, true pseudo para.

The photochlorination of fullerenes demonstrates the ability of zeolites to selectively functionalize the $C_{60}$ molecules. "Para" dichlorinated fullerenes can be formed. These "para" di-substituted fullerenes can be an important monomer precursor for synthesizing fullerene-containing polymers.

To selectively photochlorinate fullerenes in accordance with an embodiment of the invention, fullerene molecules are loaded on molecular sieve material, such as zeolite particles, from an organic solvent solution such as benzene. To accomplish this, a mixture of fullerene, zeolite particles and benzene can be allowed to stir for at least about 12 hours. Although stirring is acceptable, refluxing is a preferred loading method. Thereafter, the bulk solvent is removed and the atmosphere surrounding the fullerene loaded zeolite particles can be pumped down in a vacuum chamber, with optional heating in the range of 50°–500° C. for at least one hour for removal of residual solvent. It is preferable to pump down the chamber to between about $10^{-2}$ to $10^{-4}$ torr and heat the loaded zeolites to a temperature from 100° to 200° C. The heating step should preferably be conducted for 12 to 24 hours.

The fullerene loaded zeolite particles are then placed in a photolysis reaction chamber, such as a sealed reactor, a quartz reactor, a photochemical reactor or a fluidized bed and chlorine is introduced into the reaction chamber. The loaded zeolite particles are then photolyzed with UV radiation for up to 12 hours. Thermal chlorination would proceed in a similar manner, except that the reaction chamber would be heated rather than illuminated.

To remove the organic material including the reaction product from the zeolite particles, the photolyzed sample can be soaked in an organic solvent, such as benzene or toluene for about 12 hours, at a temperature preferably between about 25° C. and the boiling point of the extraction solvent. The solvent will then include both the unreacted fullerene starting material and the reaction product.

The products of fullerenes that are chlorinated while on molecular sieve in accordance with the invention can be subjected to analysis to confirm that the molecular sieve assisted in the selective functionalization of the fullerenes. Thermal chlorination of $C_{60}$ outside molecular sieve will yield a complex mixture of chlorinated products which will show a very broad peak at about 800–900 cm$^{-1}$. This indicates the presence of C—Cl stretching at different positions and multiple C—Cl stretching. The percentage of di-substituted and tetra-substituted fullerenes will be below 50% of the reaction product.

In contrast, the photochlorination of fullerenes that are adsorbed on zeolites yield more highly selective products of over 50% and commonly over 70% di-substituted or tetra-substituted fullerenes and will show a sharp peak at about 800 cm$^{-1}$. Thermally chlorinated $C_{60}$ adsorbed in zeolites will also produce selectively chlorinated $C_{60}$ as will be indicated by a sharp peak at 800 cm$^{-1}$ in an FT-IR spectrum.

The halogenated (such as chlorinated or brominated) products of fullerenes can undergo various chemical reactions and lead to additional selectively functionalized products. Halogen atoms on halogenated fullerenes can be replaced by methoxy groups through methoxylation. This can be confirmed by FT-IR and $^1$H NMR analysis. Halogenated products of fullerenes can also undergo dehalogenation by a reaction with triphenylphosphine. These chemical reactions confirm and help establish the extent of fullerene halogenation on zeolites. Other organic groups can be added to fullerenes in a similar manner.

Still other selective functionalization reactions can be carried out on zeolites. For example, the selective addition of amines to fullerenes yields aminated fullerenes by a single electron transfer mechanism involving radical ions. The proton form of zeolites are acid catalysts. Fullerenes undergo Friedel-Crafts reactions with aromatic hydrocarbons in the presence of acid catalysts. Accordingly, aromatic molecules such as benzene or toluene can react with fullerenes adsorbed on acid forms of zeolites. The restricted environment of zeolites will yield selective products from the controlled Friedel-Crafts reactions. The zeolite can also act as a catalyst for this reaction by serving as a proton source. Other reactions that can be carried out in zeolites to achieve controlled functionalization include hydrogenation, reaction with oxygen, alkylation and others.

Selectively functionalized fullerenes can be used as building blocks in fullerene-based materials. They can be used as monomers in the polymerization process to produce fullerene-containing polymers which can find applications in high temperature superconductors, non-linear optical materials and membrane materials that can be useful for the separation of gases.

Aspects and embodiments of the invention will be explained in greater detail with reference to the following examples. These examples are presented for purposes of illustration only and are not intended to be construed in a limiting sense.

EXAMPLE 1 (for comparison)

Figure 2:
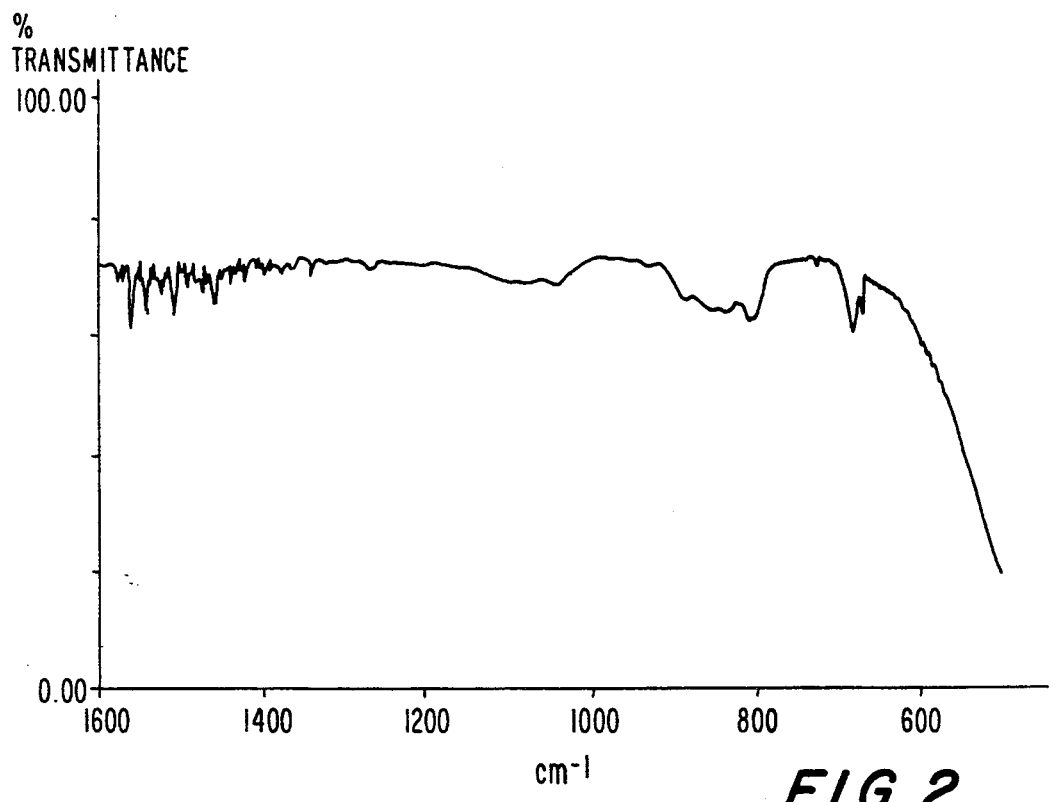
FIG. 2 is an FT-IR spectrum of $C_{60}$ which was chlorinated by a conventional thermal method.

The thermal chlorination of solid $C_{60}$ was carried out in a conventional manner as follows. 10.3 mg of $C_{60}$ was placed in a quartz tube. Chlorine gas was passed through the tube at a constant rate of 10 mL/min as the tube was heated to a temperature of 375° C. for a period of 4 hours. The tube was then allowed to cool to room temperature. Thermal chlorination was evidenced by a change in the color of $C_{60}$ from black to a deep rusty red. 30 mL of benzene was then added to the tube to dissolve the product therein and the dissolved product was subjected to analysis. The chlorinated products were deposited on NaCl plates and an FT-IR spectrum was obtained with a Perkin-Elmer FT-IR spectrometer. The results of this analysis are presented in FIG. 2 which shows that the thermal chlorination of $C_{60}$ yielded very broad overlapping peaks in the range of 800–900 cm$^{-1}$. This is consistent with published results and evidences a relatively low level of selective functionalization.

The chlorinated $C_{60}$ was dehalogenated by reacting it with triphenylphosphine. An excess amount of triphenylphosphine was added to a benzene solution of the chlorinated $C_{60}$ and the mixture was stirred for 1 hour at room temperature. Thin layer chromatography (TLC) was conducted with 5% toluene in hexanes as eluent. This showed that the disappearance of staining due to chlorinated $C_{60}$ and the appearance of staining due to regenerated $C_{60}$.

EXAMPLE 2 (for comparison)

Figure 3:
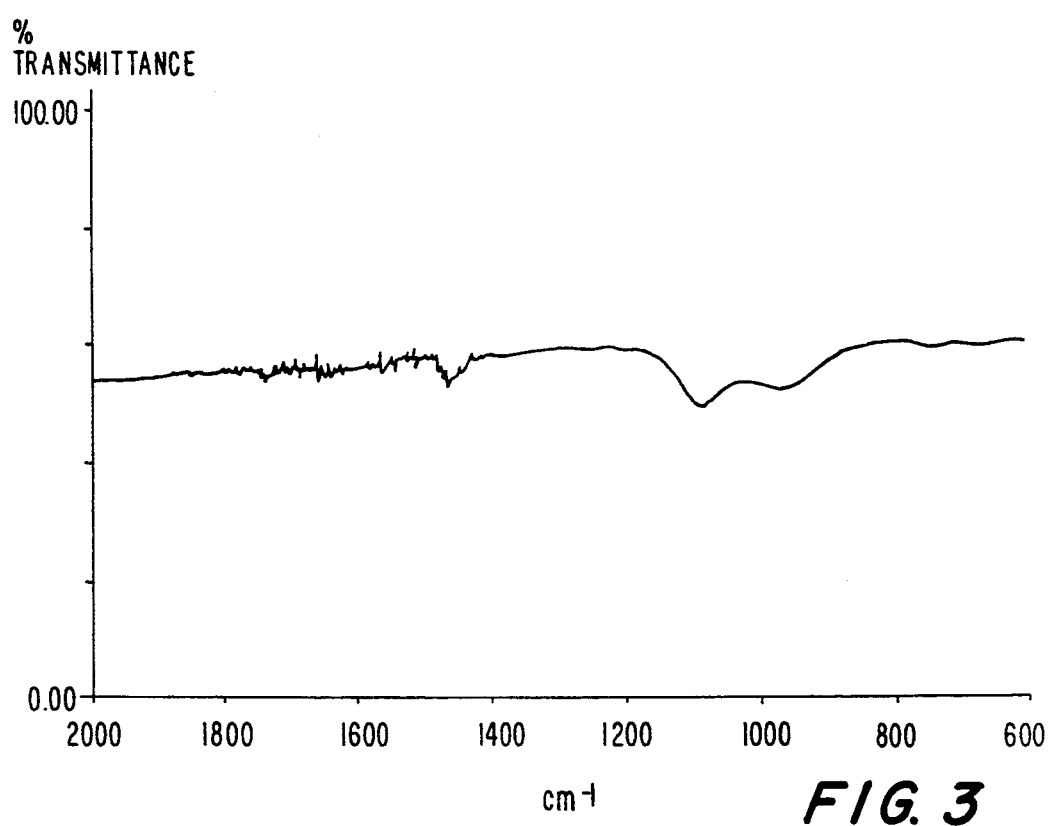
FIG. 3 is an FT-IR spectrum of the material of FIG. 2, after the product was methoxylated.
Figure 4:
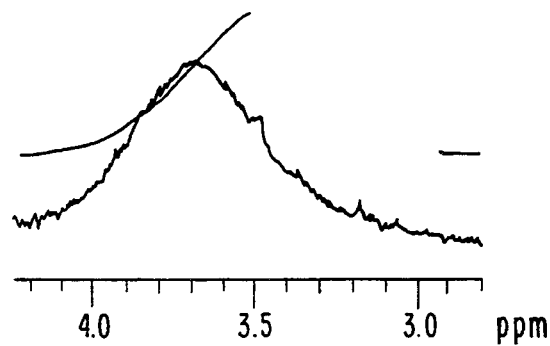
FIG. 4 is an $^1$H NMR spectrum of the methoxylated $C_{60}$ product of FIG. 3.

The chlorinated products of solid $C_{60}$ obtained from Example 1 were methoxylated with $NaOCH_3$ and $CH_3OH$ under reflux as follows. The chlorinated products from Example 1 were refluxed for 12 hours in $NaOCH_3/CH_3OH$ which was prepared by reacting 0.4 g of sodium metal with 30 mL of anhydrous $CH_3OH$. After cooling the solution to room temperature, saturated $NH_4Cl$ aqueous solution was used to quench the reaction. The solution was separated and extracted with benzene to yield methoxylated $C_{60}$. An FT-IR spectrum was prepared and is shown in FIG. 3. FIG. 3 shows the disappearance of C—Cl stretching and the appearance of a very broad peak at about 1090 $cm^{-1}$ resulting from C—O stretching. This indicates that chlorine atoms on $C_{60}$ were replaced by methoxyl groups. A $^1H$ BMR spectrum of the methoxylated $C_{60}$ was taken on a 360 MHz FT-NMR spectrometer. As shown in FIG. 4, there is a broad, structureless peak from 3.0 to 4.2 ppm resulting from the protons of methoxy groups on $C_{60}$, which indicates multiple random methoxylation on $C_{60}$.

EXAMPLE 3

Figure 5:
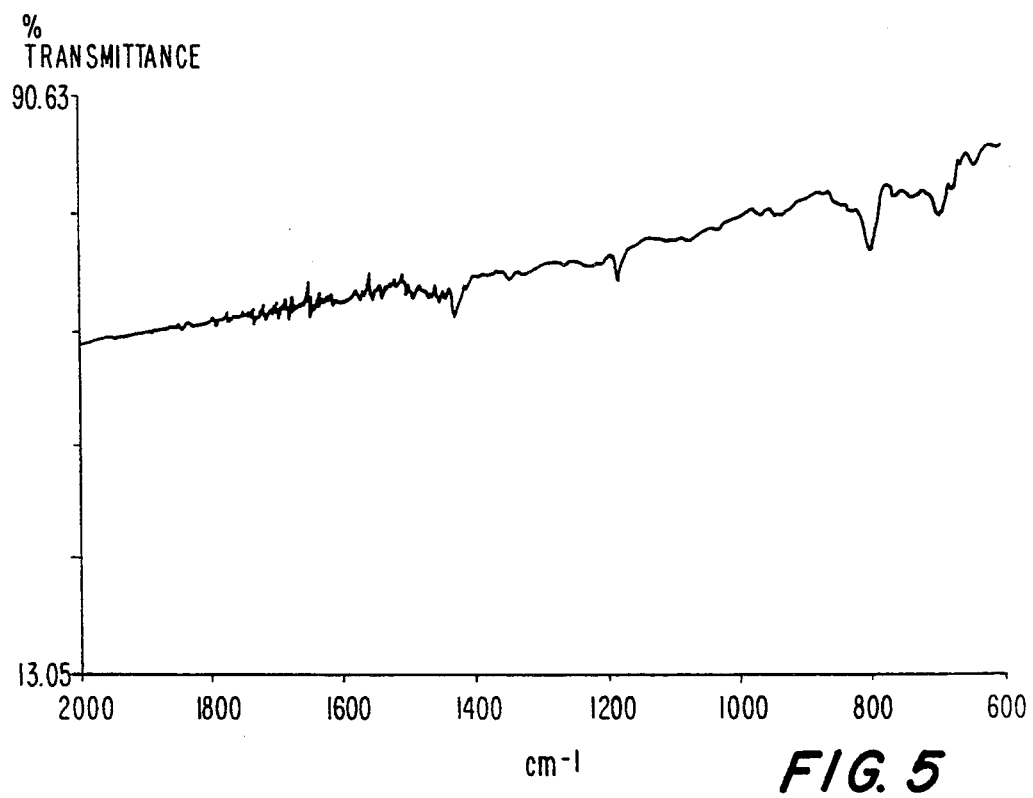
FIG. 5 is an FT-IR spectrum of photochlorinated fullerene material prepared in accordance with an embodiment of the invention.

The selective photochlorination of fullerenes on zeolite L was performed as follows. 8.4 mg of $C_{60}$ was dissolved in 40 mL of benzene. 420.3 mg of zeolite L was calcined at 550° C. for 12 hours and was added to the $C_{60}$ benzene solution. The mixture was refluxed for 12 hours under $N_2$ atmosphere and then the bulk solvent was removed. The loaded zeolite was placed in a vacuum chamber and the atmosphere surrounding the $C_{60}$ loaded zeolite sample was pumped down to $10^{-4}$ torr and heated at 120° C. for 13 hours to remove any of the residual solvent. The sample was then placed in a quartz reactor equipped with a Teflon-lined stopper and the reaction vessel was purged with nitrogen for 15 minutes, followed by purging with chlorine gas for 15 minutes. The sample was sealed and photolyzed for 4 hours with constant tumbling with a 254 nm low pressure mercury lamp. After photolysis, 40 mL of benzene was added to the reactor and refluxed for 12 hours to extract the reaction product. The chlorinated fullerene product was deposited on NaCl plates and an FT-IR spectrum was obtained with a Perkin-Elmer FT-IR spectrometer. As shown in FIG. 5 the photochlorination of $C_{60}$ on zeolite L yields a very sharp peak about 800 $cm^{-1}$ due to C—Cl stretching. The sharp peak of Example 3, compared to that of Example 1 indicates a large relative increase in selective functionalization when photochlorination is conducted on zeolites, compared to conventional methods.

The chlorinated $C_{60}$ of this example was dehalogenated by reacting it with triphenylphosphine. Excess triphenylphosphine was added to the benzene solution containing the chlorinated $C_{60}$ and the mixture was stirred for 1 hour at room temperature. Thin layer chromatography using 5% toluene in hexanes as eluent evidenced the disappearance of staining due to chlorinated $C_{60}$ and the appearance of staining due to the generated $C_{60}$. FT-IR studies showed that photochlorination of fullerenes on zeolite L yielded a much simpler product due to significantly more selective chlorination, compared to the conventional chlorination of solid fullerenes described in Example 1.

EXAMPLE 4

Figure 6:
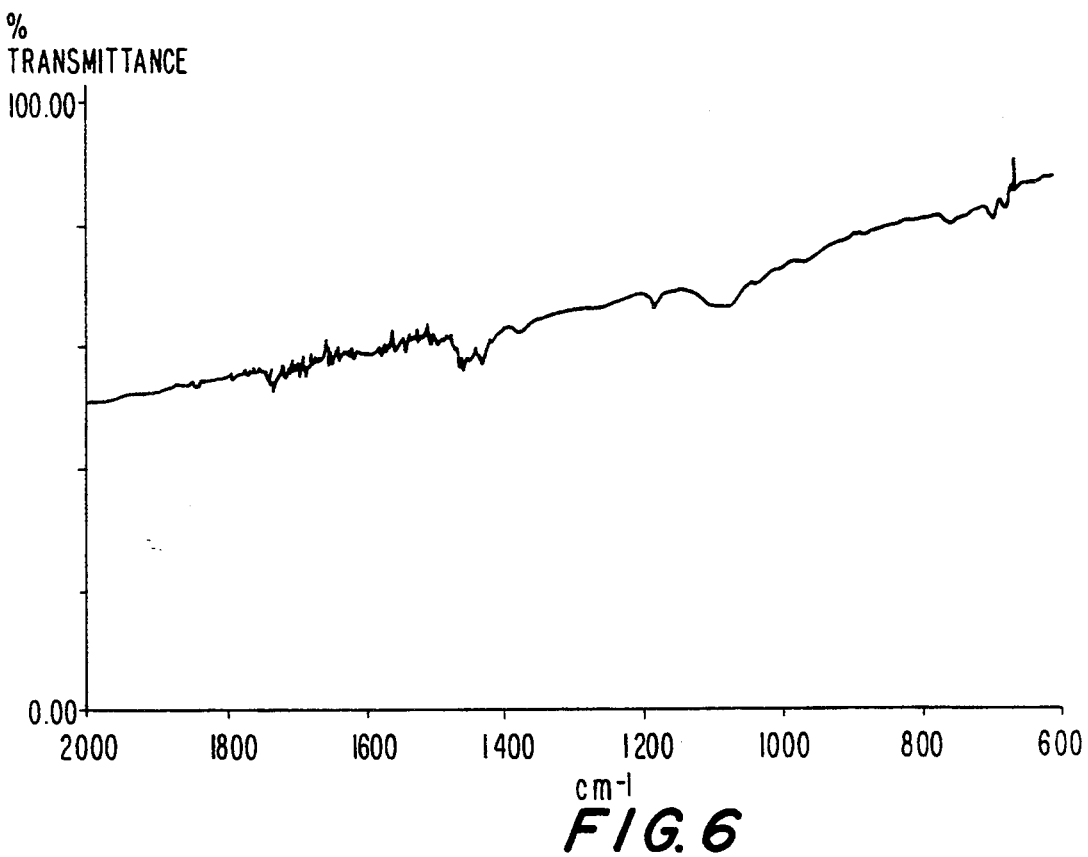
FIG. 6 is an FT-IR spectrum of the methoxylated material of FIG. 5.

Chlorinated fullerenes were converted to secondary products. The chlorinated product from Example 3 was refluxed for 12 hours in an $NaOCH_3/CH_3OH$ solution prepared by reacting 0.4 g of sodium metal with 30 mL anhydrous $CH_3OH$. After the solution was cooled to room temperature, saturated $NH_4Cl$ aqueous solution was used to quench the reaction. The reaction product was separated and extracted with benzene to yield methoxylated $C_{60}$. An FT-IR spectral analysis of the extracted product is shown in FIG. 6. FIG. 6 shows the disappearance of C—Cl stretching and the appearance of a narrow peak at about 1090 $cm^{-1}$ due to C—O stretching. This indicates that chlorine atoms on $C_{60}$ were replaced by methoxyl groups. Furthermore, the sharpness of the peak provides further evidence of the selective functionalization of the fullerene molecules on zeolite L.

Figure 7:
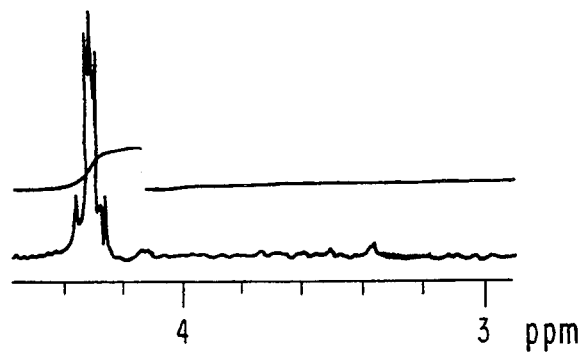
FIG. 7 is an $^1$H NMR spectrum of the methoxylated material of FIG. 6.

A $^1H$ NMR spectrum of the methoxylated $C_{60}$ was conducted. The results are shown in FIG. 7, which shows four discrete peaks at 4.3 ppm due to the protons of the methoxy groups on $C_{60}$. FIG. 7 also confirms that the photochlorination of $C_{60}$ on zeolite particles was much more selective than by the conventional method on solid $C_{60}$. The chemical shifts have a 0.5 ppm downfield shift relative to the sample in Example 2. This indicates that the fullerene structure was largely intact and again supports the conclusion that the functionalization of fullerenes on zeolites is highly selective.

EXAMPLE 5

Figure 8:
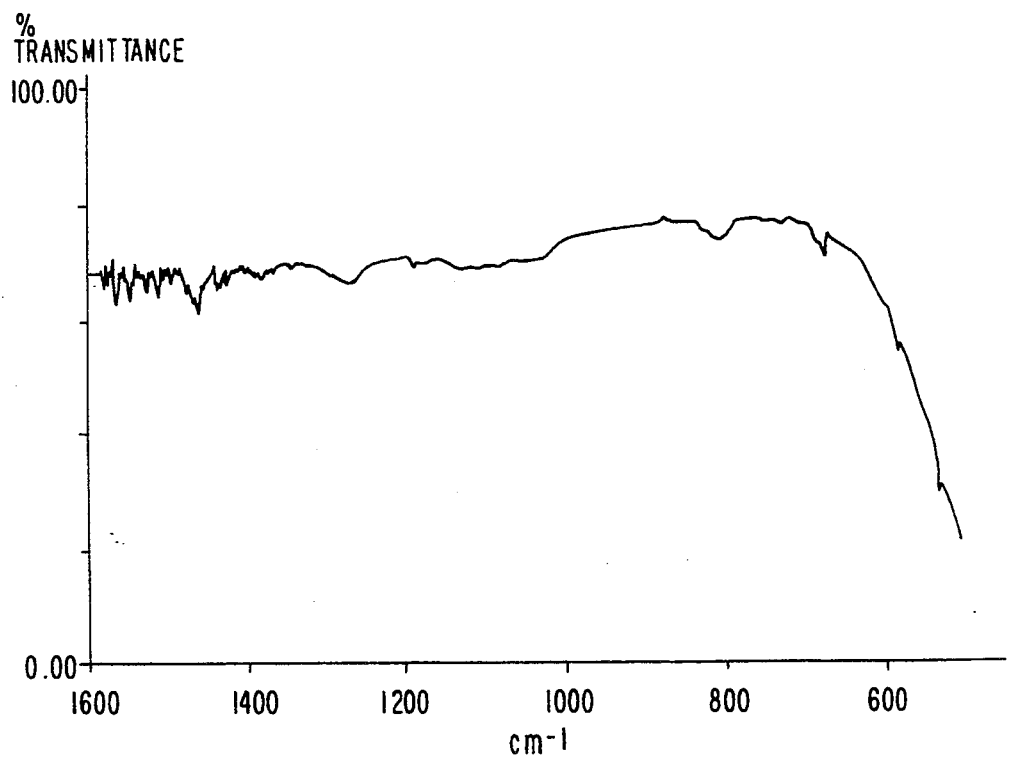
FIG. 8 is an FT-IR spectrum of photochlorinated $C_{60}$ formed in accordance with an embodiment of the invention.
Figure 9:
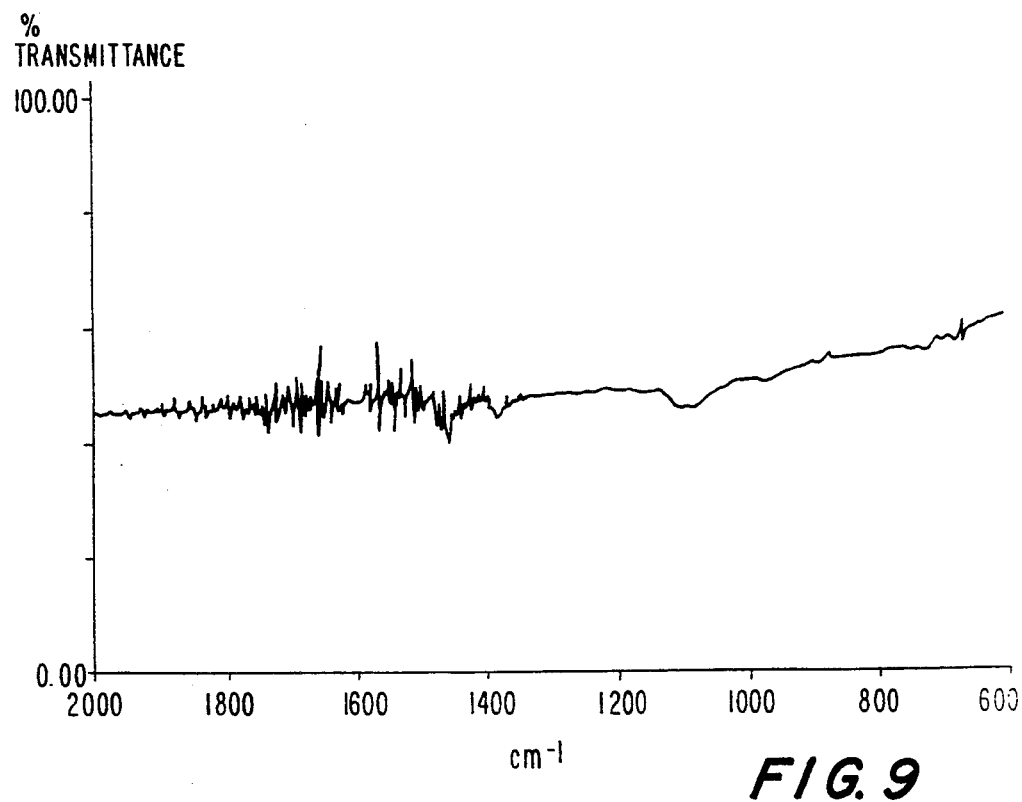
FIG. 9 is an FT-IR spectrum of the methoxylated material of FIG. 8.

The photochlorination of $C_{60}$ on a different type of molecular sieve, zeolite mordenite, was examined as follows. 5.2 mg of $C_{60}$ was dissolved in 30 mL of benzene 263.7 mg of zeolite mordenite, which has an Si:Al ratio of about 10:1 was added to the solution and the mixture was stirred for 12 hours. The bulk solvent was removed and the fullerene loaded zeolite sample was pumped down to $10^{-4}$ torr for 3 hours. The sample was then placed in a quartz reactor, which was purged with nitrogen for 5 minutes, followed by purging with chlorine gas for 5 more minutes. The reactor was then sealed and photolyzed for 6 hours with a 254 nm low pressure mercury lamp. 30 mL of benzene was added to the sample, with stirring for 12 hours, to extract the organic product. An FT-IR spectrum was obtained and is shown in FIG. 8. The spectrum shows a narrow peak at 800 $cm^{-1}$ indicating the highly selective chlorination of fullerenes on mordenite. The chlorinated $C_{60}$ was then methoxylated in substantially the same manner of Example 4 and the FT-IR spectrum of that sample showed a narrow peak at 1090 $cm^{-1}$ (FIG. 9) indicating the replacement of C—Cl by C—$OCH_3$ on $C_{60}$ and also confirmed the relatively high selective functionalization on zeolite mordenite.

EXAMPLE 6

Figure 10:
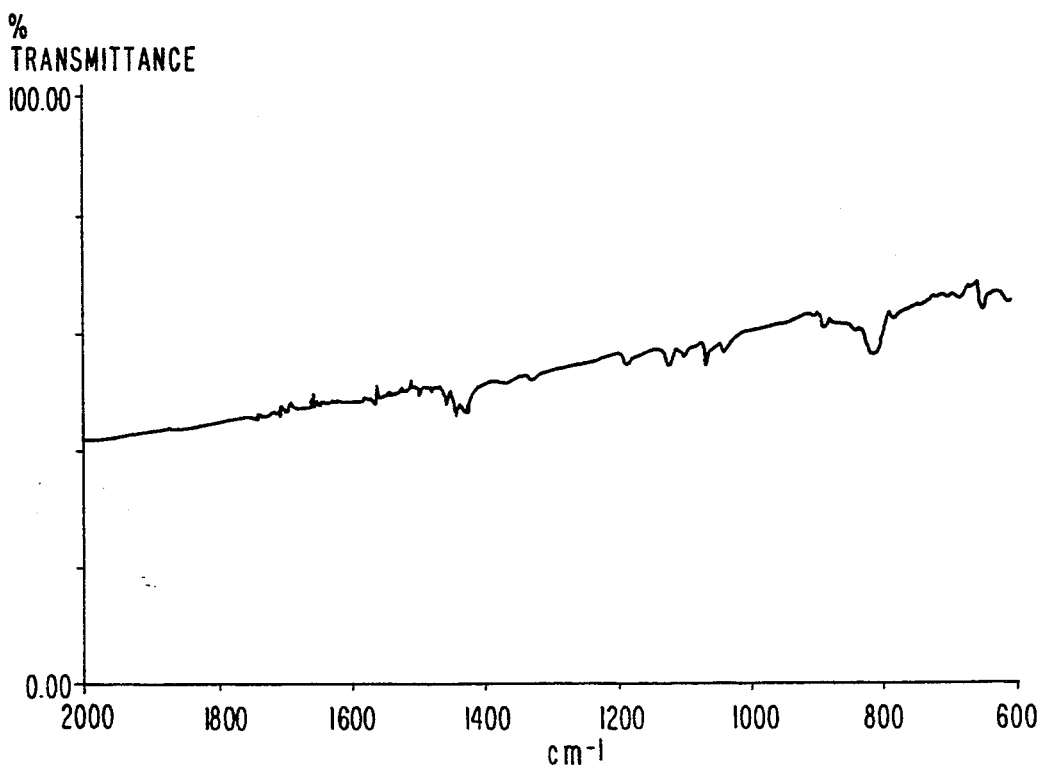
FIG. 10 is an FT-IR spectrum of photochlorinated $C_{60}$ formed in accordance with an embodiment of the invention.
Figure 11:
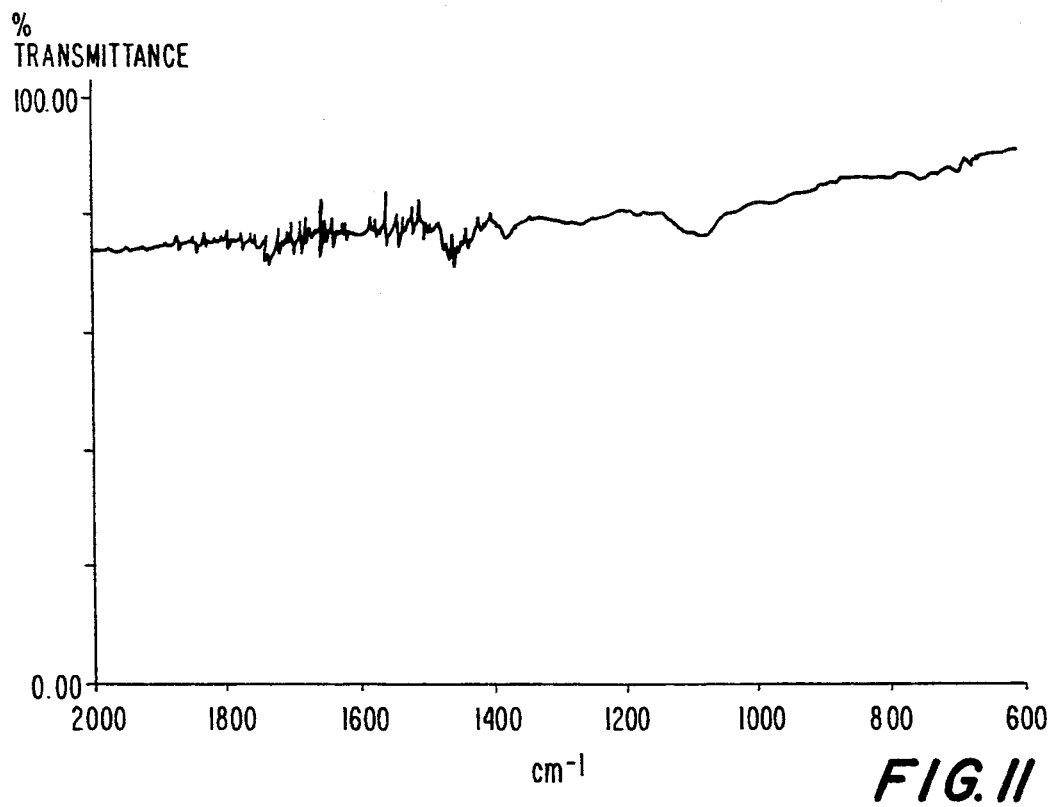
FIG. 11 is an FT-IR spectrum of the material of FIG. 10, after methoxylation.

$C_{60}$ was photochlorinated on zeolite NaY as follows. 12.2 mg of $C_{60}$ was dissolved in 50 mL benzene. 610.6 mg of zeolite NaY which has a Si:Al ratio of about 2.4:1 was added to the above solution and the mixture was stirred for 12 hours. The bulk solvent was removed and the loaded zeolite sample was pumped down to $10^{-4}$ torr for 1 hour. The sample was then placed in a quartz reactor which was purged with nitrogen for 15 minutes, followed by purging with chlorine gas for 10 minutes. The reactor was then sealed and photolyzed with a 254 nm low pressure mercury lamp for 7 hours. 60 mL of benzene was used to extract the product, after photolysis by stirring for 12 hours. The FT-IR spectrum of the sample is shown in FIG. 10 and shows a narrow peak at 800 cm$^{-1}$, which confirms the relatively high selective chlorination of $C_{60}$ on NaY zeolite. The chlorinated products of $C_{60}$ were methoxylated and an FT-IR spectrum was obtained from the product and is shown in FIG. 11. The FT-IR spectrum shows a narrow peak at 1090 cm$^{-1}$, which indicates the replacement of C—Cl by C—OCH$_3$ on $C_{60}$.

EXAMPLE 7

Figure 12:
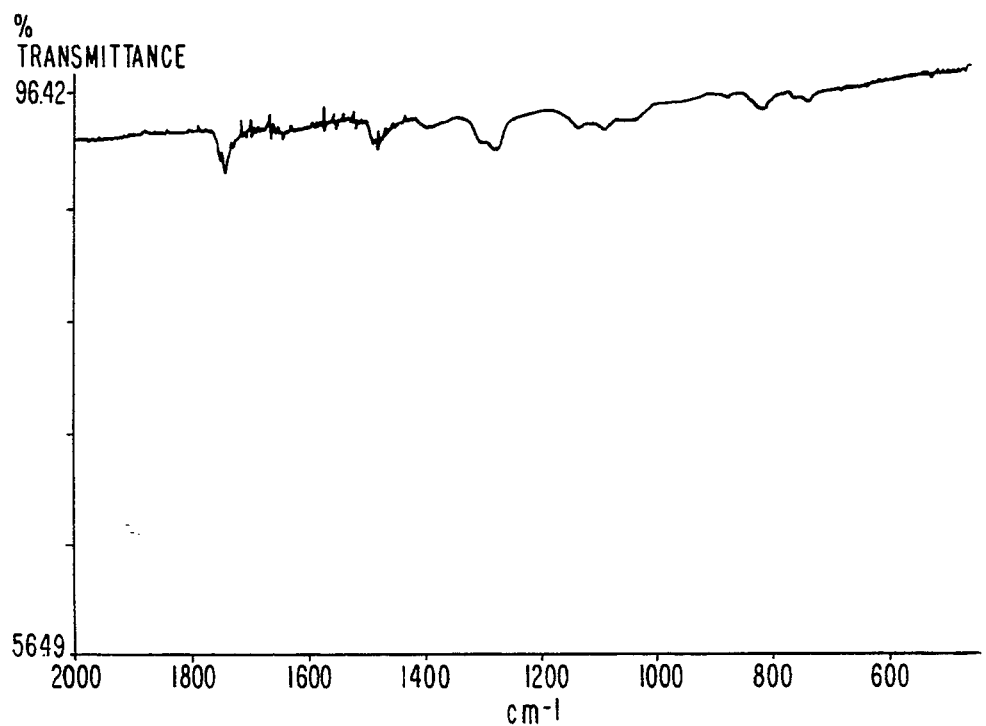
FIG. 12 is an FT-IR spectrum of thermally chlorinated $C_{60}$ formed in accordance with an embodiment of the invention.

The selective thermal chlorination of $C_{60}$ zeolite mordenite was conducted as follows. 4.9 mg of $C_{60}$ was dissolved in 30 mL benzene. 496.2 mg zeolite mordenite was calcined at 550° C. for 12 hours and then added to the $C_{60}$ benzene solution and the mixture was refluxed for 12 hours. The bulk solvent was removed and the $C_{60}$ loaded zeolite sample was pumped down to 10$^{-4}$ torr with heating at 80° C. for 12 hours. The sample was then placed in a quartz tube and a stream of chlorine gas flowing at 10 mL/min was passed through the tube for 6 hours while the tube was heated to a temperature of 400° C. The tube was agitated periodically to insure better contact between the chlorine gas and $C_{60}$ mordenite sample. After the thermal chlorination reaction was completed, 30 mL of benzene was used to extract the organic material from the zeolite particles by refluxing the benzene/zeolite mixture for 12 hours. The extracted chlorinated products were deposited on NaCl plates and an FT-IR spectrum was obtained with a Perkin-Elmer FT-IR spectrometer. As shown in FIG. 12, the thermal chlorination of $C_{60}$ on zeolite mordenite gave a very sharp peak at about 800 cm$^{-1}$ due to C—Cl stretching, indicating relatively high selective chlorination.

EXAMPLE 8

The photochlorination of $C_{60}$ adsorbed on zeolite NaY was carried out in a fluidized bed reactor as follows. 9.2 mg of $C_{60}$ was loaded on 459.8 mg of NaY as in Example 6. The loaded sample was placed in a fluidized bed reactor with nitrogen as the fluidizing gas. Chlorine gas was added to the nitrogen gas stream and the sample was photochlorinated for 60 minutes with a 254 nm low pressure mercury ultraviolet lamp. Thereafter, the reaction products were extracted with 40 mL of benzene by stirring for 12 hours. An FT-IR spectrum was obtained and it showed a narrow peak at about 795 cm$^{-1}$ indicating highly selective photochlorination.

EXAMPLE 9

Figure 13:
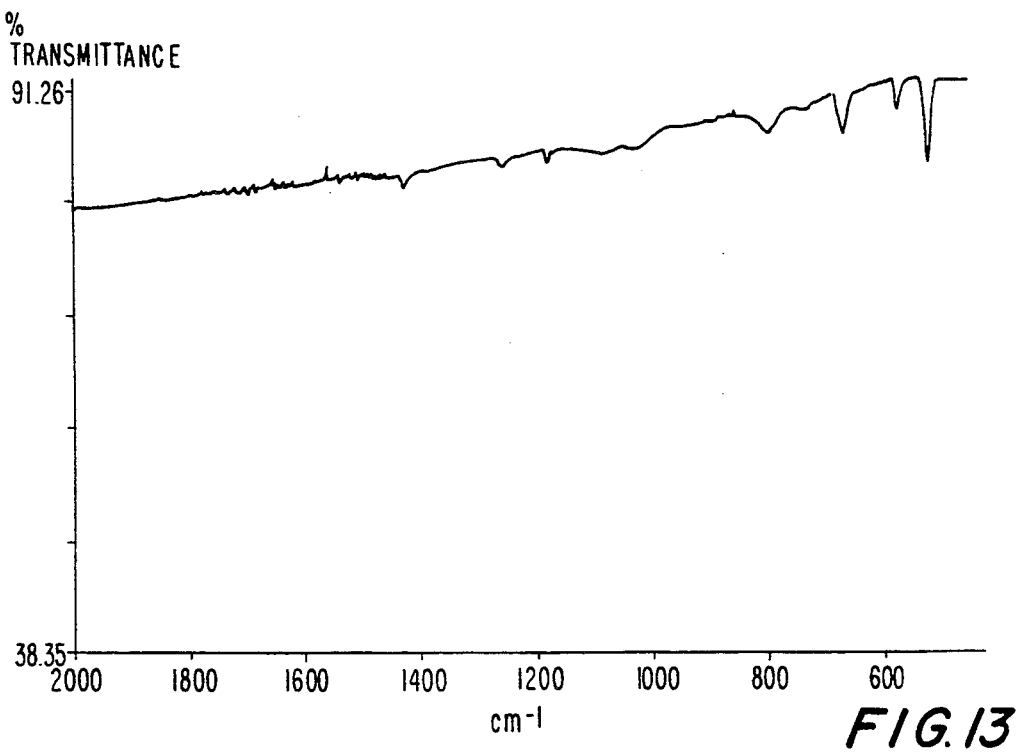
FIG. 13 is an FT-IR spectrum of photochlorinated $C_{60}$ formed in accordance with an embodiment of the invention.
Figure 14:
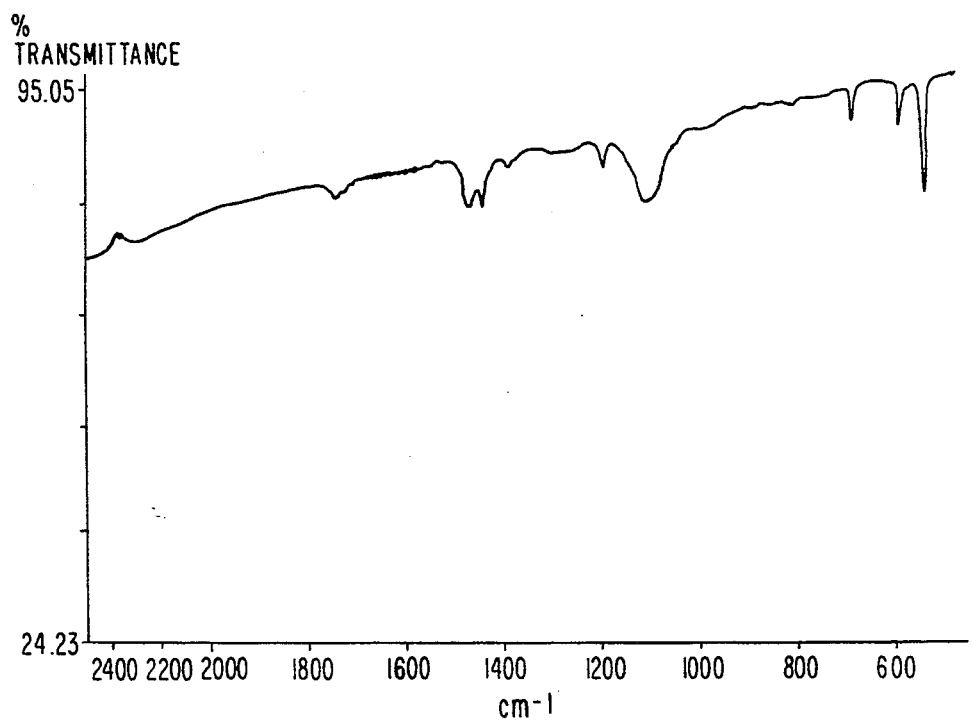
FIG. 14 is an FT-IR spectrum of the methoxylated product of FIG. 13.

$C_{60}$ was photochlorinated on ETS-10, a titanium-containing molecular sieve, as follows. 8.2 mg of $C_{60}$ was dissolved in 40 mL of benzene. 411.2 mg of ETS-10 molecular sieve, obtained from the Englehard Company, was added to the $C_{60}$ benzene solution and the mixture was refluxed for 12 hours. The bulk solvent was removed and the $C_{60}$ loaded ETS-10 sample was pumped down to 10$^{-4}$ torr with heating at 420° C. for 16 hours. The sample was then placed in a quartz reactor equipped with a Teflon ®-lined stopper and purged with nitrogen for 15 minutes, followed by purging with chlorine gas for 15 minutes. The reactor was then sealed and photolyzed for 4 hours with constant tumbling with a 254 nm light source. After photolysis was completed, 40 mL of benzene was added to the reactor to extract the reaction product, by refluxing for 12 hours. An FT-IR spectrum of the chlorinated $C_{60}$ was recorded and is shown in FIG. 13. Sharp peaks at 800 cm$^{-1}$ due to C—Cl stretching were observed, indicating relatively high selective functionalization. The product was then methoxylated and another FT-IR spectrum was obtained, as shown in FIG. 14. This spectrum shows the disappearance of C—Cl stretching and the appearance of C—O—Me stretching.

EXAMPLE 10

Figure 15:
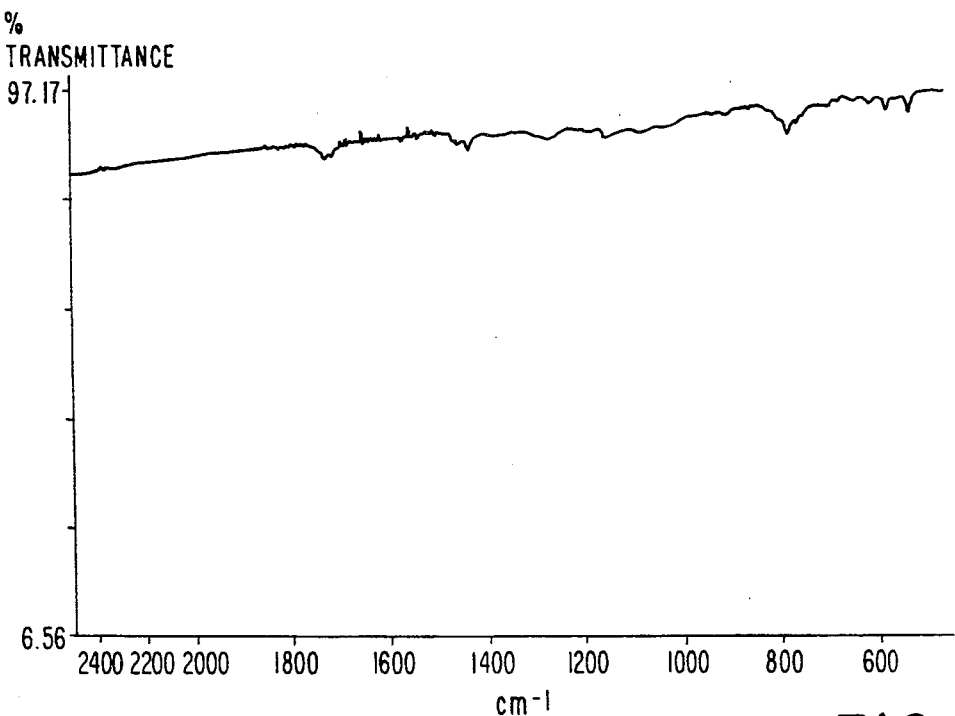
FIG. 15 is an FT-IR spectrum of brominated $C_{60}$ formed in accordance with an embodiment of the invention.

The selective bromination of $C_{60}$ adsorbed on zeolite L was conducted as follows. 7.2 mg of $C_{60}$ was dissolved in 40 mL of benzene and 361.1 mg of zeolite L was added thereto. The loaded sample was prepared as in Example 7 and placed in a reaction vessel. After purging for 15 minutes with nitrogen, 0.1 mL of bromine was added to the sample, which was then photolyzed for 4 hours with 254 nm light. The reaction product was extracted by refluxing with benzene for 12 hours and an FT-IR spectrum was recorded on a KBr plate. The spectrum is shown in FIG. 15, which shows sharp peaks at 780 cm$^{-1}$, 764 cm$^{-1}$ and 536 cm$^{-1}$, indicating relatively high selective bromination of $C_{60}$.

EXAMPLE 11

Figure 16:
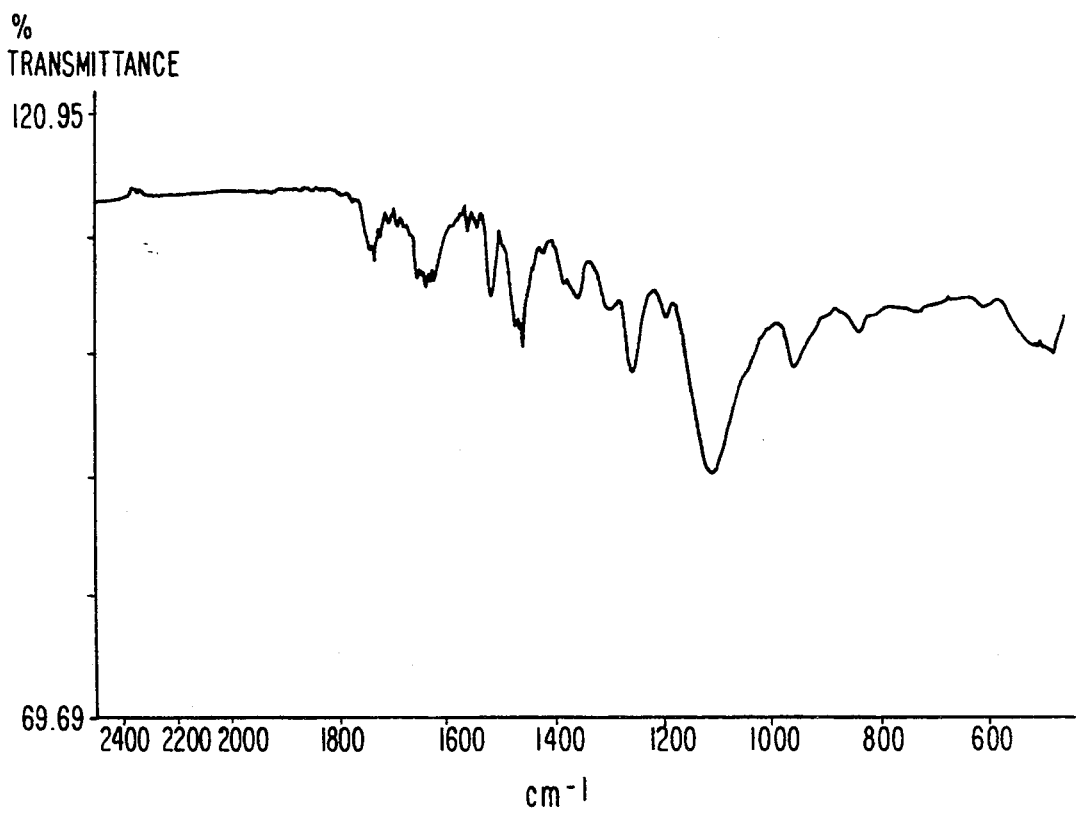
FIG. 16 is an FT-IR spectrum of the product of FIG. 15, after methoxylation.

The brominated $C_{60}$ sample obtained in Example 10 was refluxed for 12 hours in NaOCH$_3$/CH$_3$OH, which was prepared by reacting 0.4 g of sodium metal with 30 mL of anhydrous CH$_3$OH to yield methoxylated $C_{60}$ was in Example 4. As shown in FIG. 16, an FT-IR spectrum was obtained and shows the disappearance of peaks due to C—Br stretching at 780 cm$^{-1}$, 764 cm$^{-1}$ and 536 cm$^{1}$. The appearance of a single narrow peak at 1090 cm$^{-1}$ in FIG. 16 indicates the replacement of C—Br by C—OCH$_3$.

It was concluded, based in part on FT-IR and $^1$H NMR analyses of the functionalized fullerene product, that yields of greater than 50% and even 70% purity can be obtained with a method and reactor in accordance with embodiments of the invention. More than 50% and even more than 70% of the chlorinated product can be di-substituted or tetra-substituted molecules. Due to the large size of bromine atoms, the majority of the brominated product will be di-substituted.

It will thus be seen that the objects set forth above, among those made apparent from the preceding description, are efficiently attained and, since certain changes may be made in carrying out the above method, in the compositions and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of functionalizing fullerene molecules, comprising the steps of:

providing both molecular sieve material having controlled spaces therein;

sorbing fullerene material into the molecular sieve material, including into the controlled spaces thereof, to yield a quantity of fullerene loaded molecular sieve material;

chemically reacting a reactant material with the fullerene molecules of the fullerene loaded molecular sieve material to yield functionalized fullerene reaction product within the controlled spaces.

2. The method of claim 1, wherein the fullerene material is sorbed into the molecular sieve material by dissolving the fullerene material in a solvent, combining the solvent and fullerene solution with the molecular sieve for an effective amount of time to permit the incorporation of fullerene within the controlled spaces of the molecular sieve and then removing the solvent from the molecular sieve and fullerene material.

3. The method of claim 2, wherein the fullerene, solvent and molecular sieve are kept together for at least 12 hours after being combined.

4. The method of claim 2, wherein the mixture of solvent, fullerene and molecular sieve is stirred or refluxed for 12 hours.

5. The method of claim 1, wherein the solvent is one of benzene and toluene.

6. The method of claim 1, wherein the molecular sieve includes zeolite material.

7. The method of claim 2, wherein the molecular sieve is zeolite material.

8. The method of claim 6, wherein the zeolite material is selected from the group consisting of NaX, NaY, mordenite, zeolite L and combinations thereof.

9. The method of claim 1, wherein the molecular sieve material includes silicalite.

10. The method of claim 1, wherein the reaction yielding functionalized fullerene material includes a photoinitiation step.

11. The method of claim 1, wherein the reaction yielding functionalized fullerene material is a chlorination reaction.

12. The method of claim 11, wherein the chlorination reaction is thermally initiated.

13. The method of claim 11, wherein the chlorination reaction is photoinitiated.

14. The method of claim 10, wherein the wavelength of irradiation for the photoinitiation step is between about 200 nm and 700 nm.

15. The method of claim 12, wherein the thermal initiation step includes heating fullerene loaded molecular sieve to a temperature of between about 50° C. and 900° C.

16. The method of claim 1, wherein the reaction yielding fuctionalized fullerene material is a bromination reaction.

17. The method of claim 16, wherein the bromination reaction includes a photoinitiation step.

18. The method of claim 16, wherein the wavelength of irradiation for the photoinitiation step of the reaction is between about 200 nm and 700 nm.

19. The method of claim 16, wherein the bromination reaction includes a thermal initiation step.

20. The method of claim 19, wherein the temperature of temperature of the thermal initiation step is between about 25° C. and 400° C. and 400° C.

21. The method of claim 1, including the step of adding an amine to the fullerene during the reaction yielding functionalized fullerene reaction product.

22. The method of claim 1, including the step of adding a free radical species to the fullerene during the reaction yielding functionalized fullerene reaction product.

23. The method of claim 1, including the step of copolymerization of free radical species with the fullerene during the reaction yielding functionalized fullerene reaction product.

24. The method of claim 1, including the step of conducting a Friedel-Crafts reactions of fullerene with aromatic organic compounds during the reaction yielding functionalized fullerene reaction product.

25. The method of claim 1, wherein the fullerene is halogenated during the reaction yielding functionalize fullerene reaction product and then the halogen is substituted for a different compound or group.

26. The method of claim 2, wherein the substitution is performed by conducting a methoxylation reaction.

27. The method of claim 1, wherein the controlled spaces are 7 to 18 Å large.

28. A composition comprising chlorinated fullerene material, characterized by a sharp peak at about 800 $cm^{-1}$ in an FT-IR spectrum.

29. The composition of claim 28, wherein the chlorinated fullerene material is more than about 50% di-substituted and tetra-substituted chlorinated fullerene material.

30. The composition of claim 28, wherein the chlorinated fullerene material is more than about 70% di-substituted and tetra-substituted chlorinated fullerene material.

31. A composition comprising brominated fullerene material characterized by sharp peaks at 780, 764 and 536 $cm^{-1}$ in an FT-IR spectrum.

32. The composition of claim 31, wherein the brominated fullerene material is at least 50% di-brominated fullerene.

33. A composition comprising functionalized fullerene material, in which at least 70% of the composition is no more than 2 different species.

* * * * *